(12) United States Patent
Yang (10) Patent No.: US 9,751,082 B1
(45) Date of Patent: Sep. 5, 2017

(54) MULTI-ACTUATED MICRO-PIPETTE CONTROLLER AND ASSOCIATED USE THEREOF

(71) Applicant: Dunsong Yang, Jacksonville, FL (US)

(72) Inventor: Dunsong Yang, Jacksonville, FL (US)

( * ) Notice: Subject to any disclaimer, the term of this patent is extended or adjusted under 35 U.S.C. 154(b) by 27 days.

(21) Appl. No.: 14/720,699

(22) Filed: May 22, 2015

Related U.S. Application Data (60) Provisional application No. 62/001,665, filed on May 22, 2014.

(51) Int. Cl.
*B01L 3/02* (2006.01)
*A61B 17/43* (2006.01)

(52) U.S. Cl.
CPC .............. *B01L 3/021* (2013.01); *A61B 17/43* (2013.01); *B01L 3/0275* (2013.01); *B01L 2200/027* (2013.01); *B01L 2400/0481* (2013.01)

(58) Field of Classification Search
CPC ...................................................... B01L 3/021
See application file for complete search history.

(56) References Cited

U.S. PATENT DOCUMENTS

| | | | |
|---|---|---|---|
| 4,784,834 A | 11/1988 | Hirschmann | |
| 5,154,702 A * | 10/1992 | Foyil | B01L 3/0282 215/214 |
| 5,445,797 A | 8/1995 | Flesher | |
| 2009/0227833 A1 | 9/2009 | Arabia et al. | |
| 2012/0003129 A1 | 1/2012 | Rempt et al. | |
| 2014/0020789 A1* | 1/2014 | Duquet | A45D 34/04 141/24 |

* cited by examiner

*Primary Examiner* — Paul Hyun
(74) *Attorney, Agent, or Firm* — Ashkan Najafi (57) ABSTRACT

A multi-actuated micro-pipette controller is actuated in at least three different ways. First, the multi-actuated micro-pipette controller may be employed similar to a striper for denudation of cumulus cells and transfer of oocytes and embryos by depressing an actuator assembly operably coupled to a ballonet. Second, the multi-actuated micro-pipette controller may be actuated similar to a SWEMED™ denudation pipette by pressing directly on the ballonet while it is seated in a primary housing and a secondary housing, without employing an actuator assembly of the primary housing. Third, the multi-actuated micro-pipette controller may be actuated by removing the ballonet and employing it similar to a PASTEUR™ pipette.

19 Claims, 10 Drawing Sheets

MULTI-ACTUATED MICRO-PIPETTE CONTROLLER AND ASSOCIATED USE THEREOF

CROSS REFERENCE TO RELATED APPLICATIONS

This application claims the benefit of U.S. Provisional Application No. 62/001,665 filed May 22, 2014, the entire disclosures of which are incorporated herein by reference.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF NON-LIMITING EXEMPLARY EMBODIMENT(S) OF THE PRESENT DISCLOSURE

Technical Field

Exemplary embodiment(s) of the present disclosure relate to pipettes for use micro-manipulation procedures and, more particularly, to a multi-actuated micro-pipette controller having a plurality of operating modes for selectively transporting fluid in a succinct and ergonomic manner.

Prior Art

Micro-pipettes are often used for in vitro fertilization (IVF) procedures such as denuding/cleaning of cumulus cell around oocytes, transfer of gametes and embryos which are required for intracytoplasmic sperm injection (ICSI), embryo biopsy, assisted hatching, oocytes and embryo assessment, culture and other related procedures. Such procedures are often performed in an embryology lab using conventional micro-pipettes employing a squeeze bulb end connected to a glass/plastic tip with a very small diameter. To promote consistency and accuracy, controllers are used in combination with micro-pipettes. One conventional controller is a pistol mechanism for micro-pipetting. Such a controller has several shortcomings because its interior is not sterile, although some can be autoclaved. Other conventional controllers have a very small control volume and cannot create large suction force for denudation of cells around oocyte. Further, other conventional controllers require close placement of the operator's hand to the tip of the micro-pipette tip, which makes it difficult to operate.

Accordingly, a need remains for a multi-actuated micro-pipette controller in order to overcome at least one prior art shortcoming. The exemplary embodiment(s) satisfy such a need by providing a multi-actuated micro-pipette controller that is convenient and easy to use, lightweight yet durable in design, versatile in its applications, and designed for having a plurality of operating modes to selectively transport fluid in a succinct and ergonomic manner.

BRIEF SUMMARY OF NON-LIMITING EXEMPLARY EMBODIMENT(S) OF THE PRESENT DISCLOSURE

In view of the foregoing background, it is therefore an object of the non-limiting exemplary embodiment(s) to provide a multi-actuated micro-pipette controller having a plurality of operating modes for selectively transporting a volume of fluid. These and other objects, features, and advantages of the non-limiting exemplary embodiment(s) are provided by a multi-actuated micro-pipette controller including a primary housing including a proximal end and a distal end axially opposed therefrom, a primary access port formed adjacent to the distal end, and a chamber extending from the proximal end to the distal end such that the chamber is accessible from the primary access port.

The multi-actuated micro-pipette controller further includes a secondary housing removably seated within the chamber. Such a secondary housing has a secondary access port at least partially aligned with the primary access port. A ballonet is adapted to receive the fluid therein. Such a ballonet is removably inserted within the secondary housing and at least partially aligned with the secondary access port such that the ballonet is directly accessible and squeezable via the primary access port and the secondary access port.

The multi-actuated micro-pipette controller further includes an actuator assembly located at the primary housing and being operably engaged with the ballonet. Advantageously, linear actuation of the actuator assembly compresses at least a portion of the ballonet and thereby causes the fluid to expel outwardly from the ballonet. Notably, the secondary housing is coaxially aligned with the primary housing while the secondary housing is disposed within the chamber.

In a non-limiting exemplary embodiment, the secondary housing is linearly inserted and retracted from the chamber of the primary housing during non-operating conditions.

In a non-limiting exemplary embodiment, the secondary housing remains statically nested within the chamber of the primary housing while the ballonet is compressed and released between tension and equilibrium positions, respectively.

In a non-limiting exemplary embodiment, the multi-actuated micro-pipette controller further includes a micro-pipette tip removably inserted into the proximal end of the primary housing and being in fluid communication with the ballonet.

In a non-limiting exemplary embodiment, when the ballonet and the secondary housing are operably removed from the chamber of the primary housing, the ballonet and the secondary housing are operably disengaged from the actuator assembly such that the fluid is discharged outwardly away from the secondary housing by directly squeezing the ballonet seated exterior of the primary housing.

In a non-limiting exemplary embodiment, when the ballonet is operably removed from the secondary housing, the fluid is discharged outwardly away from the ballonet by directly squeezing the ballonet seated exterior of both the primary housing and the secondary housing. In this manner, the ballonet and the secondary housing are operably disengaged from the actuator assembly.

In a non-limiting exemplary embodiment, the primary access port and the secondary access port overlap along the longitudinal length of the primary housing.

In a non-limiting exemplary embodiment, the secondary housing remains spaced from the actuator assembly while the secondary housing and the ballonet are seated within the chamber of the primary housing.

In a non-limiting exemplary embodiment, the actuator assembly and the ballonet are oriented at an end-to-end configuration while seated within the chamber of the primary housing.

The present disclosure further includes a method of utilizing a multi-actuated micro-pipette controller for selectively transporting a volume of fluid. Such a method includes the steps of: obtaining a primary housing including a proximal end and a distal end axially opposed therefrom, a primary access port formed adjacent to the distal end, and a chamber extending from the proximal end to the distal end such that the chamber is accessible from the primary access port; and obtaining and removably seating a secondary housing within the chamber wherein the secondary housing has a secondary access port at least partially aligned with the primary access port. Notably, the secondary housing is coaxially aligned with the primary housing while the secondary housing is disposed within the chamber.

The method further includes the steps of: obtaining a ballonet adapted to receive the fluid therein; removably inserting the ballonet within the secondary housing and at least partially aligning the ballonet with the secondary access port such that the ballonet is directly accessible and squeezable via the primary access port and the secondary access port; obtaining and locating an actuator assembly at the primary housing; operably engaging the actuator assembly with the ballonet; and causing the fluid to expel outwardly from the ballonet by linearly actuating the actuator assembly and thereby compressing at least a portion of the ballonet.

There has thus been outlined, rather broadly, the more important features of non-limiting exemplary embodiment(s) of the present disclosure so that the following detailed description may be better understood, and that the present contribution to the relevant art(s) may be better appreciated. There are additional features of the non-limiting exemplary embodiment(s) of the present disclosure that will be described hereinafter and which will form the subject matter of the claims appended hereto.

BRIEF DESCRIPTION OF THE NON-LIMITING EXEMPLARY DRAWINGS

The novel features believed to be characteristic of non-limiting exemplary embodiment(s) of the present disclosure are set forth with particularity in the appended claims. The non-limiting exemplary embodiment(s) of the present disclosure itself, however, both as to its organization and method of operation, together with further objects and advantages thereof, may best be understood by reference to the following description taken in connection with the accompanying drawings in which:

Those skilled in the art will appreciate that the figures are not intended to be drawn to any particular scale; nor are the figures intended to illustrate every non-limiting exemplary embodiment(s) of the present disclosure. The present disclosure is not limited to any particular non-limiting exemplary embodiment(s) depicted in the figures nor the shapes, relative sizes or proportions shown in the figures.

DETAILED DESCRIPTION OF NON-LIMITING EXEMPLARY EMBODIMENT(S) OF THE PRESENT DISCLOSURE

The present disclosure will now be described more fully hereinafter with reference to the accompanying drawings, in which non-limiting exemplary embodiment(s) of the present disclosure is shown. The present disclosure may, however, be embodied in many different forms and should not be construed as limited to the non-limiting exemplary embodiment(s) set forth herein. Rather, such non-limiting exemplary embodiment(s) are provided so that this application will be thorough and complete, and will fully convey the true spirit and scope of the present disclosure to those skilled in the relevant art(s). Like numbers refer to like elements throughout the figures.

The illustrations of the non-limiting exemplary embodiment(s) described herein are intended to provide a general understanding of the structure of the present disclosure. The illustrations are not intended to serve as a complete description of all of the elements and features of the structures, systems and/or methods described herein. Other non-limiting exemplary embodiment(s) may be apparent to those of ordinary skill in the relevant art(s) upon reviewing the disclosure. Other non-limiting exemplary embodiment(s) may be utilized and derived from the disclosure such that structural, logical substitutions and changes may be made without departing from the true spirit and scope of the present disclosure. Additionally, the illustrations are merely representational are to be regarded as illustrative rather than restrictive.

One or more embodiment(s) of the disclosure may be referred to herein, individually and/or collectively, by the term "non-limiting exemplary embodiment(s)" merely for convenience and without intending to voluntarily limit the true spirit and scope of this application to any particular non-limiting exemplary embodiment(s) or inventive concept. Moreover, although specific embodiment(s) have been illustrated and described herein, it should be appreciated that any subsequent arrangement designed to achieve the same or similar purpose may be substituted for the specific embodiment(s) shown. This disclosure is intended to cover any and all subsequent adaptations or variations of other embodiment(s). Combinations of the above embodiment(s), and other embodiment(s) not specifically described herein, will be apparent to those of skill in the relevant art(s) upon reviewing the description.

References in the specification to "one embodiment(s)", "an embodiment(s)", "a preferred embodiment(s)", "an alternative embodiment(s)" and similar phrases mean that a particular feature, structure, or characteristic described in connection with the embodiment(s) is included in at least an embodiment(s) of the non-limiting exemplary embodiment(s). The appearances of the phrase "non-limiting exemplary embodiment" in various places in the specification are not necessarily all meant to refer to the same embodiment(s).

Directional and/or relationary terms such as, but not limited to, left, right, nadir, apex, top, bottom, vertical, horizontal, back, front and lateral are relative to each other and are dependent on the specific orientation of an applicable element or article, and are used accordingly to aid in the description of the various embodiment(s) and are not necessarily intended to be construed as limiting.

The non-limiting exemplary embodiment(s) is/are referred to generally in FIGS. 1-4 and is/are intended to provide a multi-actuated micro-pipette controller 10 includes a hand-held housing 11 including an access door 12 pivotally attached thereto via a gemel 19. Gemel 19 interlocks with at least one receiving aperture 22 formed at housing 11 and an inner surface of access door 12 thereby maintaining a pivot connection between housing 11 and access door 12. Thus, access door 12 is hingedly articulated relative to housing 11. A slide button 20 is linearly reciprocated along an outer surface of the access door 12. Slide button 20 has at least one finger penetrating through access door 12 and interlocks with a slide lock 21 disposed along an inner surface of access door 12. Slide lock 21 has finger locks 36 protruding inwardly from the inner surface of access door 12. In this manner, when access door 12 is closed and slide button 20 is linearly displaced to a locked position, finger locks 36 engage tabs 31 and prevent access door 12 from disengaging housing 11. When the slide button 20 is linearly displaced to an unlocked position, finger locks 36 disengage tabs 31 and permit access door 12 to pivot open relative to housing 11. In this manner, locking mechanism 20-21 may be linearly actuated along a travel path generally parallel to a longitudinal length of the housing. Of course, various types of locking mechanisms may be employed without departing from the true spirit and scope of the disclosure.

In a non-limiting exemplary embodiment, as shown in FIGS. 1-4, a chamber 45 is located within housing 11 and is suitable sized and shaped for receiving, generally midway between axially opposed proximal and distal ends of the housing 11, a ballonet stand 28. Of course, the ballonet stand 28 may be seated at various locations defined along a longitudinal length of chamber 45. Ballonet 18, (e.g. squeeze bulb, bellow or other similar component), is seated within ballonet stand 24. An opening 42 is centrally located within a depression 28 formed in access door 12. In this manner, a portion of ballonet 18 protrudes outwardly through opening 42 when access door 12 is closed, thereby enabling a user to actuate ballonet 18 during operating procedures.

In a non-limiting exemplary embodiment, as shown in FIGS. 1-4, pin base 23 is located at a distal end of housing 12 and may partially extend exterior thereof. A connection tube 25 in intermediately coupled to ballonet 18 and pin base 23. Spring 17 is engaged with a proximal end of ballonet 18 inside housing 12. A distal end of rectilinear press pole 15 is seated within housing 12 and maintains abutment with spring 17. A stop 16 is statically fitted about press pole 15 thereby prohibiting spring 17 from displacing along an entire longitudinal length of press pole 15. A proximal end of press pole 15 protrudes outwardly from housing 12 and passes through end cap 26. Press cap 26 is fitted over the proximal end of press pole 15. A micro-pipette tip 14 is coupled to pin base 23 and sits exterior of housing 11.

In a non-limiting exemplary embodiment, as shown in FIGS. 1-4, guides 37, 38 are registered about a linear travel path defined along central longitudinal axes 39, 40 of housing 11 and access door 12, respectively. Such guides 37, 38 facilitate central alignment of press pole 15, ballonet 18, connection tube 25 and pin base 23 during use.

In a non-limiting exemplary embodiment, as shown in FIGS. 1-4, press pole 15 defines a first actuator linearly reciprocated via press cap 26. Such linear reciprocation squeezes ballonet 18 thereby causing suction/discharge of air and/or fluid via micro-pipette tip 14. The linear reciprocation occurs along a travel path defined parallel to the longitudinal axis 39 of housing 12 thereby causes air/fluid to ingress/egress therefrom micro-pipette tip 14. In this manner, an operator may suction/expel fluid via the micro-pipette tip 14 by selectively depressing only the first actuator (press pole 15)

In a non-limiting exemplary embodiment, as shown in FIGS. 1-4, opening 42 defines a second actuator by permitting direct access to ballonet 18 without depressing press cap 27. In particular, a user squeezes ballonet 18 with his/her finger. Such a squeezing motion occurs along a travel path defined substantially transverse to the longitudinal axis 39 of housing 12 thereby causing air and/or fluid to ingress/egress therefrom micro-pipette tip 14. In this manner, an operator may suction/expel fluid via the micro-pipette tip 14 by selectively depressing only the second actuator (bulbous protrusion at proximal tip of ballonet 18).

In a non-limiting exemplary embodiment, as shown in FIGS. 1-4, the ballonet 18, connection tube 25, pin base 23 and micro-pipette tip 14 can be removed from the controller 10 and independently operated by squeezing ballonet 18 without use of the first or second actuators.

Referring to FIGS. 5-14 in general, in a non-limiting exemplary embodiment, a multi-actuated micro-pipette controller 200 is provided, which can be actuated in at least three different ways. First, the multi-actuated micro-pipette controller 200 may be employed similar to a striper for denudation of cumulus cells and transfer of oocytes and embryos by depressing an actuator assembly 211 operably coupled to a ballonet 203, both of which are contained in a primary housing 201. Second, the multi-actuated micro-pipette controller 200 may be actuated similar to a SWEMED™ denudation pipette by pressing directly on the ballonet 203 while it is seated in the primary housing 201 and a secondary housing 202, without employing the actuator assembly 211 of the primary housing 201. Third, the multi-actuated micro-pipette controller 200 may be actuated by removing the ballonet 203 from the primary housing 201 and secondary housing 202 and employing it similar to a PASTEUR™ pipette.

In the first example above, the ballonet 203 is retained within the primary housing 201 and secondary housing 202. In the second example above, the ballonet 203 may be (optionally) removed from the primary housing 201 and retained within the secondary housing 202 161. In the third example, the ballonet 203 is removed from each of the primary housing 201 and secondary housing 202.

In a non-limiting exemplary embodiment, the multi-actuated micro-pipette controller 200 includes the primary housing 201 including a proximal end 204 and a distal end 205 axially opposed therefrom, a primary access port 207 formed adjacent to the distal end 205, and a chamber 206 extending from the proximal end 204 to the distal end 205 such that the chamber 206 is accessible from the primary access port 207.

The multi-actuated micro-pipette controller 200 further includes secondary housing 202 removably seated within the chamber 206. Such a secondary housing 202 has a secondary access port 208 at least partially aligned with the primary access port 207. The ballonet 203 is adapted to receive the fluid 209 therein. Such a ballonet 203 is removably inserted within the secondary housing 202 and at least partially aligned with the secondary access port 208 such that the ballonet 203 is directly accessible and squeezable via the primary access port 207 and the secondary access port 208. In this manner, the ballonet 203 and secondary housing 202 remain disposed within the primary housing 201 during use.

The multi-actuated micro-pipette controller 200 further includes an actuator assembly 211 located at the primary housing 201. Such an actuator assembly 211 is operably engaged with the ballonet 203. Advantageously, linear reciprocating displacement of the actuator assembly 211 compresses at least a proximal portion of the ballonet 203 and thereby causes the fluid 209 to expel outwardly from a distal tip of ballonet 203. Notably, the secondary housing 202 is coaxially aligned with the primary housing 201 while the secondary housing 202 is disposed within the chamber 206. Such coaxial alignment insures the actuator assembly 211 adequately engages and maintains contact with the ballonet 203.

In a non-limiting exemplary embodiment, the secondary housing 202 is linearly inserted and retracted from the chamber 206 of the primary housing 201 during non-operating conditions. In this manner, a user is able to remove the secondary housing 202 and ballonet 203 without disrupting a position of the actuator assembly 211.

In a non-limiting exemplary embodiment, the secondary housing 202 remains statically nested within the chamber 206 of the primary housing 201 while the ballonet 203 is compressed and released between tension and equilibrium positions, respectively. In this manner, a user is able to directly press, with his/her fingers, the ballonet 203 via the primary access port 207 and secondary access port 208.

In a non-limiting exemplary embodiment, the multi-actuated micro-pipette controller 200 further includes a micro-pipette tip (similar to tip 14 shown in FIGS. 1-4) removably inserted into the proximal end 204 of the primary housing 201 and being in fluid 209 communication with the ballonet 203. Such a tip may maintain a friction fit engagement with an orifice 271 formed at pin base 214.

Figure 13:
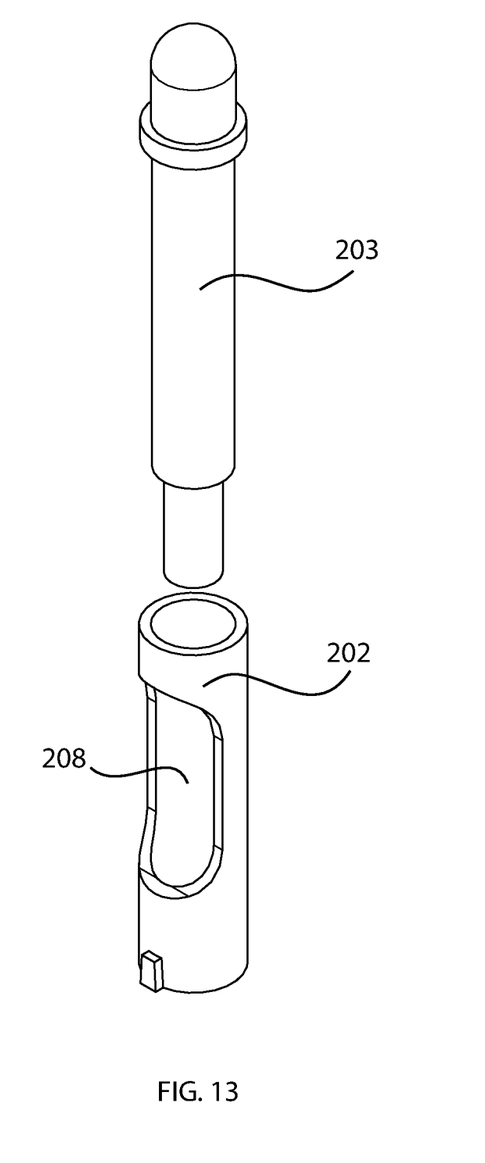
FIG. 13 is an exploded view illustrating a second operating mode wherein the ballonet and secondary housing are removed from primary housing, and thereby independently employed from the actuator assembly.

In a non-limiting exemplary embodiment, as best shown in FIG. 13, when the ballonet 203 and the secondary housing 202 are operably removed from the chamber 206 of the primary housing 201, the ballonet 203 and the secondary housing 202 are operably disengaged from the actuator assembly 211 such that the fluid 209 is discharged outwardly away from the secondary housing 202 by directly squeezing the ballonet 203 seated exterior of the primary housing 201.

Figure 14:
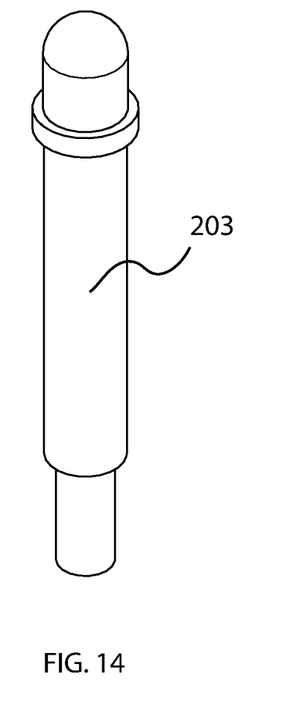
FIG. 14 is a perspective view illustrating a third operating mode wherein the ballonet is removed from primary housing and secondary housing, and thereby independently employed from the actuator assembly.

In a non-limiting exemplary embodiment, as best shown in FIG. 14, when the ballonet 203 is operably removed from the secondary housing 202, the fluid 209 is discharged outwardly away from the ballonet 203 by directly squeezing the ballonet 203 seated exterior of both the primary housing 201 and the secondary housing 202. In this manner, the ballonet 203 and the secondary housing 202 are operably disengaged from the actuator assembly 211.

In a non-limiting exemplary embodiment, the primary access port 207 and the secondary access port 208 overlap along the longitudinal length 212 of the primary housing 201. Such a structural configuration permits a user to directly squeeze the ballonet 203 from an exterior of the primary housing 201 without employing actuator assembly 211.

In a non-limiting exemplary embodiment, the secondary housing 202 remains spaced from the actuator assembly 211 while the secondary housing 202 and the ballonet 203 are seated within the chamber 206 of the primary housing 201. Such a structural configuration ensures only the proximal tip of the ballonet 203 is compressed without undesirably displacing the secondary housing 202 out of coaxial alignment with respect to the primary housing 201.

In a non-limiting exemplary embodiment, the actuator assembly 211 and the ballonet 203 are oriented at an end-to-end configuration while seated within the chamber 206 of the primary housing 201.

The present disclosure further includes a method of utilizing a multi-actuated micro-pipette controller 200 for selectively transporting a volume of fluid 209. Such a method includes the steps of: obtaining a primary housing 201 including a proximal end 204 and a distal end 205 axially opposed therefrom, a primary access port 207 formed adjacent to the distal end 205, and a chamber 206 extending from the proximal end 204 to the distal end 205 such that the chamber 206 is accessible from the primary access port 207; and obtaining and removably seating a secondary housing 202 within the chamber 206 wherein the secondary housing 202 has a secondary access port 208 at least partially aligned with the primary access port 207. Notably, the secondary housing 202 is coaxially aligned with the primary housing 201 while the secondary housing 202 is disposed within the chamber 206.

The method further includes the steps of: obtaining a ballonet 203 adapted to receive the fluid 209 therein; removably inserting the ballonet 203 within the secondary housing 202 and at least partially aligning the ballonet 203 with the secondary access port 208 such that the ballonet 203 is directly accessible and squeezable via the primary access port 207 and the secondary access port 208; obtaining and locating an actuator assembly 211 at the primary housing 201; operably engaging the actuator assembly 211 with the ballonet 203; and causing the fluid 209 to expel outwardly from the ballonet 203 by linearly actuating the actuator assembly 211 and thereby compressing at least a portion of the ballonet 203.

In a non-limiting exemplary embodiment, the primary housing 201 may have a generally tubular shape ergonomically sized to be manually hand-operated by a user.

In a non-limiting exemplary embodiment, the first access port 207 and second access port 208 are preferably located adjacent to the distal end 205 of the primary housing 201 and is suitably sized and shaped to receive a user metacarpal thereat.

Still referring to FIGS. 5-14, chamber 206 preferably extends along an entire longitudinal length L1 of primary housing 201. A major longitudinal length L2 of the ballonet 203 is directly accessible through the primary access port 207 and secondary access port 208. Of course, the ballonet 203 and both access ports 207, 208 may be seated at various locations defined along the longitudinal length L1 of chamber 206. In this manner, a portion (L2) of ballonet 203 is exposed via the access ports 207, 208, thereby enabling a user to directly actuate ballonet 203 without employing the built-in actuator assembly 211 of the primary housing 201.

In a non-limiting exemplary embodiment, as shown in FIGS. 5-14, secondary housing 202 is slidably interfitted within the chamber 206 and seated along the primary access port 207. Such a secondary housing 202 has associated secondary access port 208 wherein the ballonet 203 linearly passes through an axial bore 272 formed within the secondary housing 202. A portion (L2) of the ballonet 203 is visible and directly accessible via the secondary access port 208. In this manner, the primary access port 207 and secondary access port 208 are preferably aligned along longitudinal axis 234 of the chamber 206. At least a portion of the primary access port 207 overlaps with the secondary access port 208 thereby providing direct and unobstructed access to the ballonet 203. During operating conditions, in on mode of operation, the secondary housing 202 remains statically seated within the chamber 206 of the primary housing 201.

In a non-limiting exemplary embodiment, a pin base 223 is located at distal end 205 of housing 112 and may be threadably mated thereto. The pin base 223 has axial orifice 271 formed therein for receiving a micro-pipette tip (e.g., similar to tip 14) therethrough. The micro-pipette tip is coupled to pin base 223 in a conventional manner and sits exterior of primary housing 201. Such a micro-pipette tip is in fluid communication with ballonet 203 for discharging and receiving the fluid.

In a non-limiting exemplary embodiment, as shown in FIGS. 5-14, the actuator assembly 211 includes a helical spring 217 having a distal end engaged with a first shoulder 272 (or stop) formed in chamber 206. A proximal end of the spring 117 is engaged with a second shoulder 273 formed at the press-pole 275. Stop 272 is statically fitted about press pole 275 thereby prohibiting spring 117 from displacing beyond a distal end of the press pole 115. In this manner, the chamber 206 may be considered as a bifurcated region having a proximal section 206A and a distal section 206B.

In a non-limiting exemplary embodiment, the spring 217 is linearly biased between compressed and equilibrium positions when press-pole 275 is linearly reciprocated along a linear travel path passing through a juncture 206C of the proximal section 206A and distal section 206B of the chamber. Accordingly, the press pole 275 is registered parallel to the longitudinal axis 234 of the chamber 206. The spring 217 is compressed and released between tensioned and equilibrium positions by pressing and releasing press cap 226. Notably, the secondary housing 202 maintains a fixed spatial relationship with the primary housing 201 while the press-pole 275 is linearly reciprocated within the primary housing 201. Such a structural arrangement maintains the ballonet 203 proximal tip at a substantially stable position to be repeatedly compressed and released via the press pole 275, as needed.

In a non-limiting exemplary embodiment, the proximal end of ballonet 203 is disposed exterior of secondary housing 203 and thereby remains exposed to selectively receive the distal end of press pole 275 during actuation of the actuator assembly 211. The distal end of rectilinear press pole 275 traverses juncture 206C during its linear reciprocating motion and may maintain direct abutment with the proximal tip of ballonet 203. A proximal end of press pole 275 protrudes outwardly from primary housing 201 and passes through end cap 233. Press cap 226 is fitted over the proximal end of press pole 275 and remains partially exposed exterior of end cap 233 such that linear reciprocation of press cap 226 displaces the press-pole 275 and compresses the ballonet 203 axially aligned within primary housing 201. Such compression urges fluid 209 and air out from the micro-pipette tip as needed. Notably, ballonet 203 is not linearly displaced within chamber 206, thereby maintaining a fixed position with respect to the longitudinal length L1 of the primary housing 201. While ballonet 203 can be squeezed while seated within both the primary housing 201 and secondary housing 202, the ballonet 203 is not intended to be linearly displaced within the chamber 206 during actuation of the actuator assembly 211. Such a structural configuration facilitates proper axial aligned between the ballonet 203 and press-pole 275 during repeated use.

In a non-limiting exemplary embodiment, as shown in FIGS. 5-14, press pole 275 defines a first actuator linearly reciprocated via press cap 226. Such linear reciprocation squeezes ballonet 203 thereby causing suction/discharge of air and/or fluid 209 via a conventional micro-pipette tip. The linear reciprocation occurs along a travel path defined parallel to the longitudinal axis 234 of primary housing 201 thereby causing air/fluid 209 to ingress/egress therefrom micro-pipette tip. In this manner, a user may suction/expel fluid 209 via the micro-pipette tip by selectively depressing only the first actuator (e.g., press pole 275).

Figure 1:
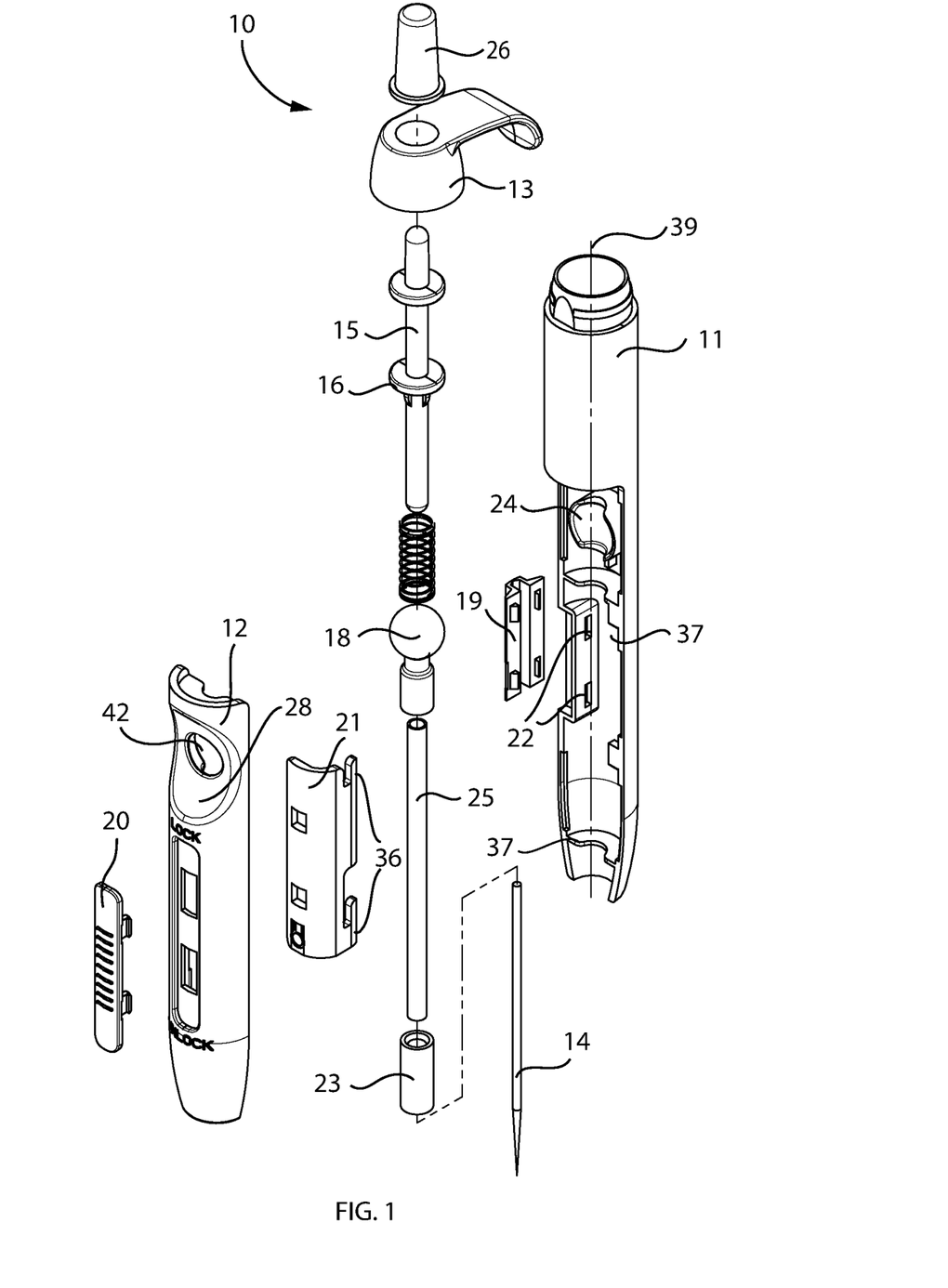
FIG. 1 is an exploded view of a multi-actuated micro-pipette controller, in accordance with a non-limiting exemplary embodiment of the present disclosure.
Figure 2:
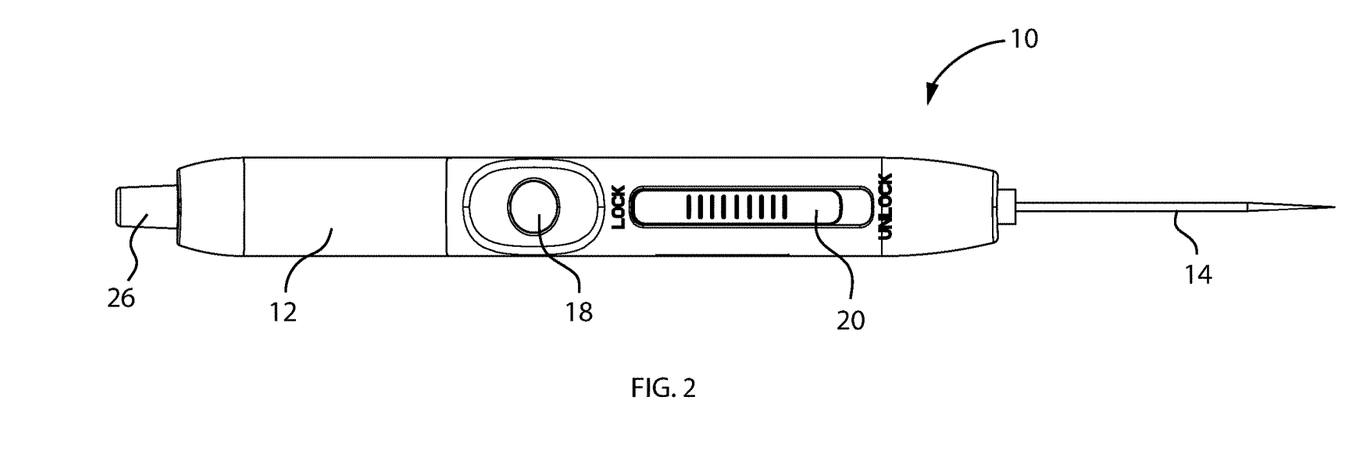
FIG. 2 is a top plan view of an assembled multi-actuated micro-pipette controller illustrated in FIG. 1.
Figure 3:
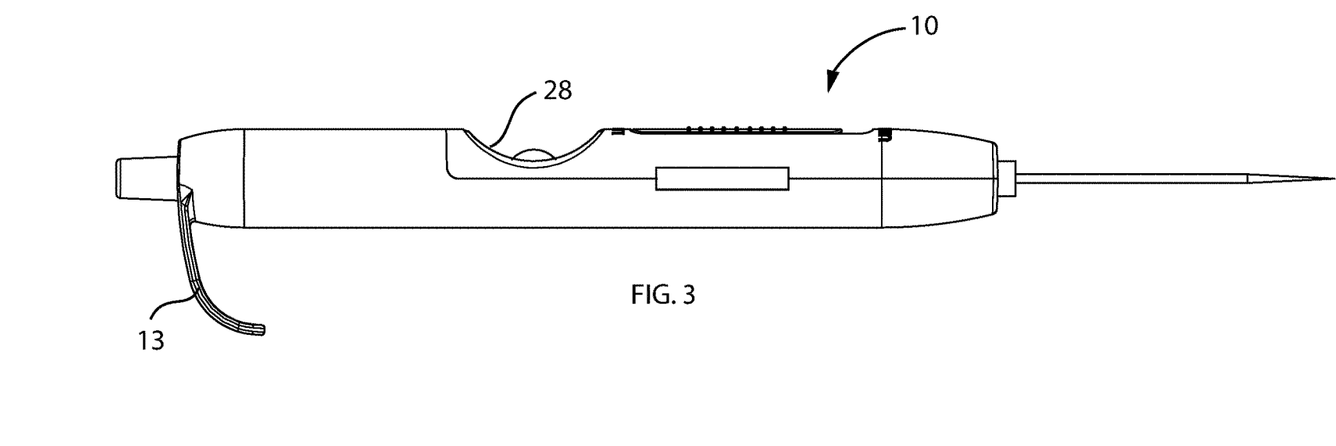
FIG. 3 is a side elevational view of an assembled multi-actuated micro-pipette controller illustrated in FIG. 1.
Figure 4:
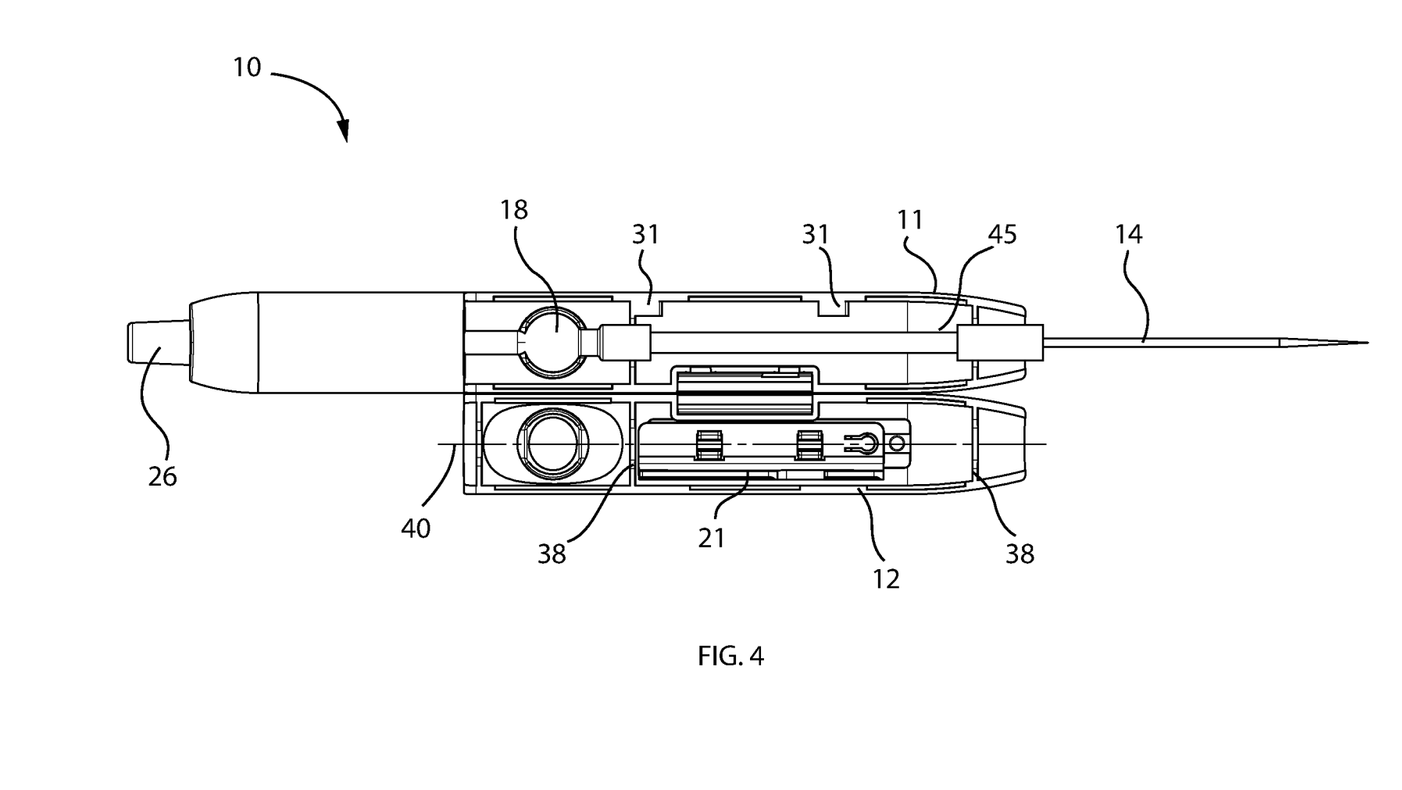
FIG. 4 is a top plan view of an assembled multi-actuated micro-pipette controller illustrated in FIG. 2, wherein the access door is biased to an open position.
Figure 5:
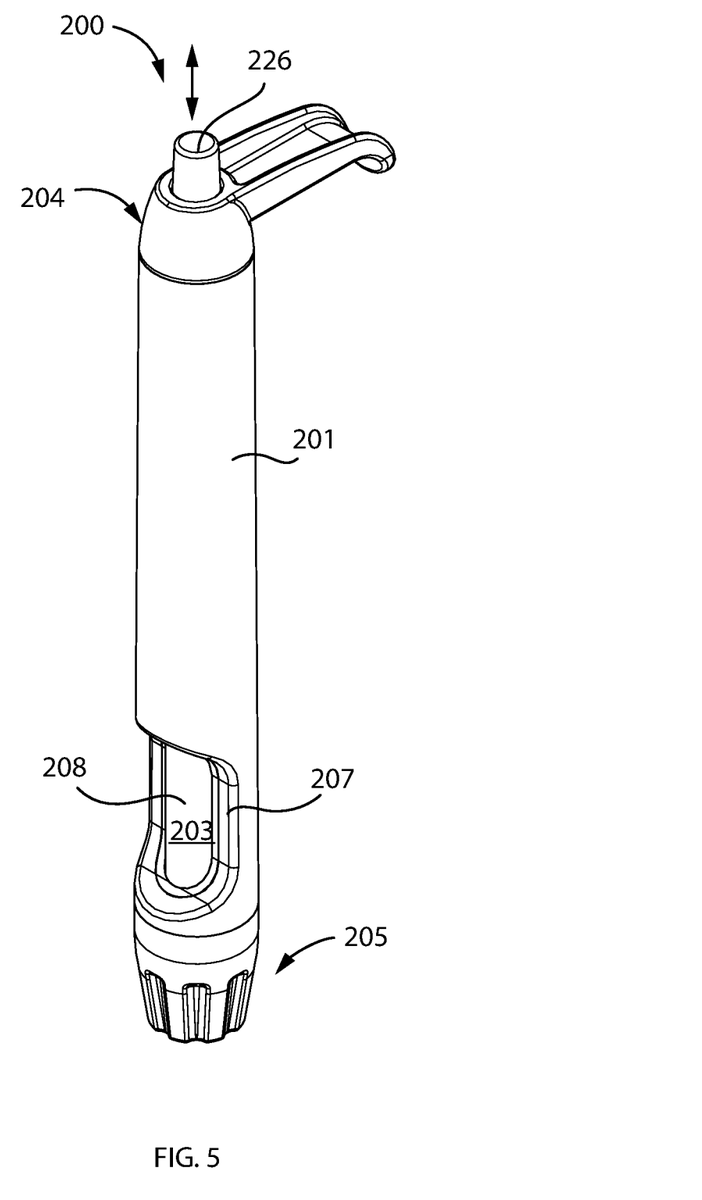
FIG. 5 is a perspective view of a multi-actuated micro-pipette controller, at a first operating mode, in accordance with another non-limiting exemplary embodiment of the present disclosure.
Figure 6:
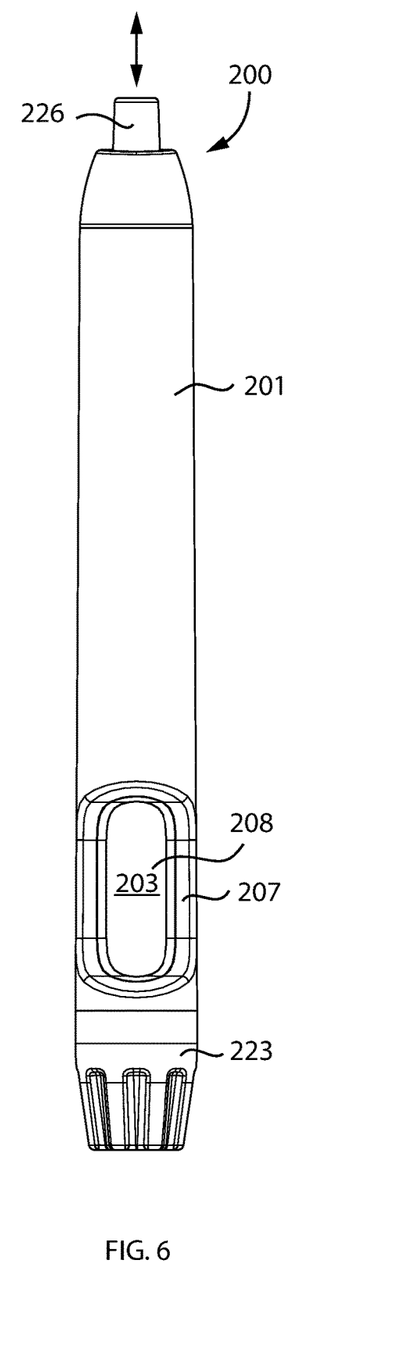
FIG. 6 is a front elevational view of the multi-actuated micro-pipette controller illustrated in FIG. 5.
Figure 7:
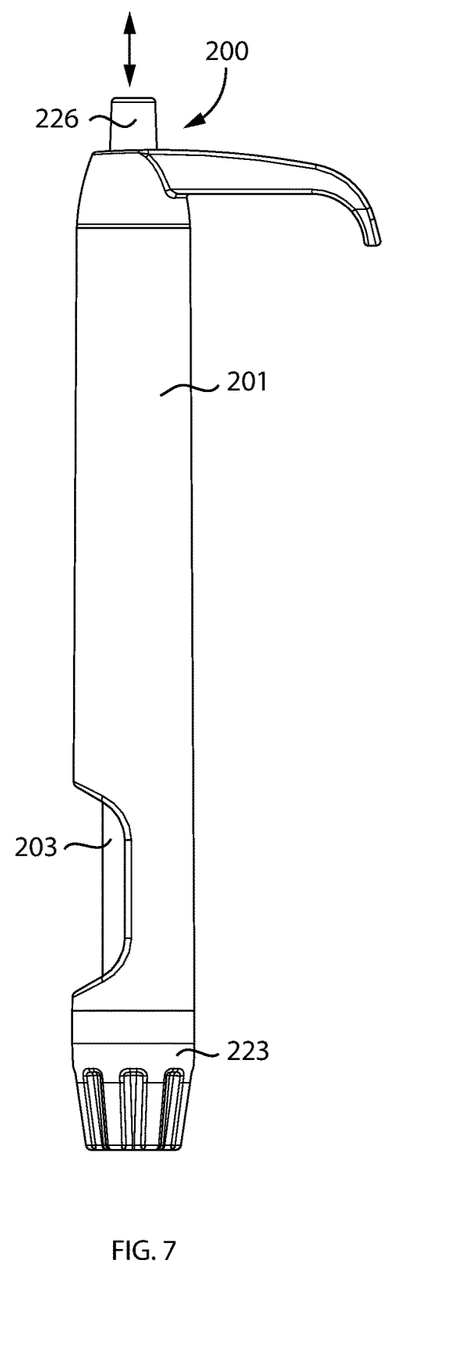
FIG. 7 is a side elevational view of the multi-actuated micro-pipette controller illustrated in FIG. 5.
Figure 8:
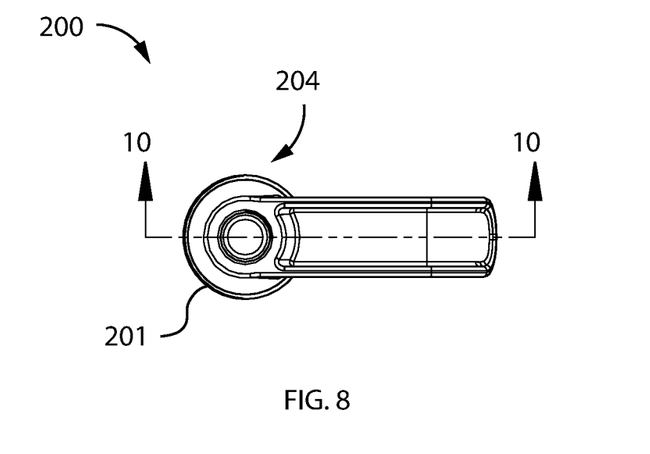
FIG. 8 is a top plan view of the multi-actuated micro-pipette controller illustrated in FIG. 5.
Figure 9:
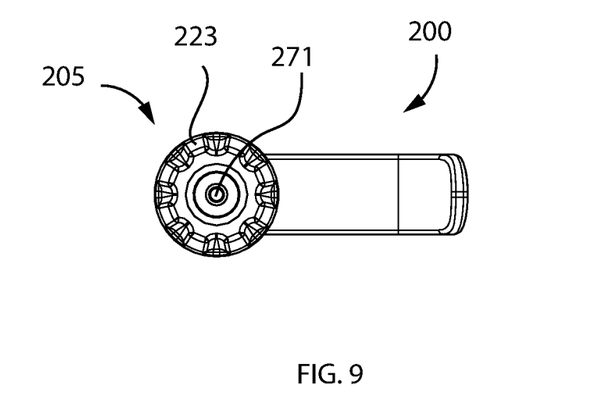
FIG. 9 is a bottom plan view of the multi-actuated micro-pipette controller illustrated in FIG. 5.
Figure 10:
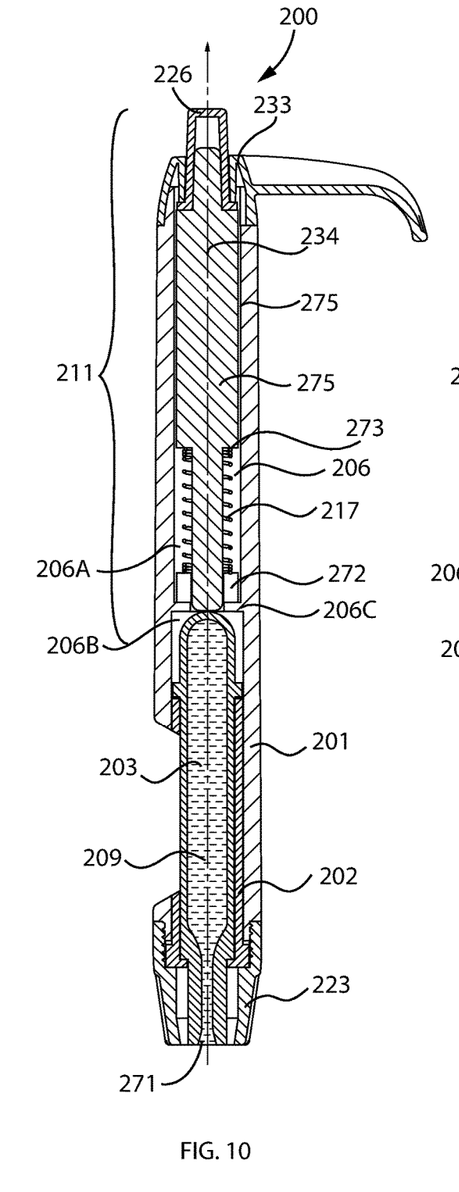
FIG. 10 is a cross-sectional view taken along line 10-10 in FIG. 8, wherein the actuator assembly is not a depressed position.
Figure 11:
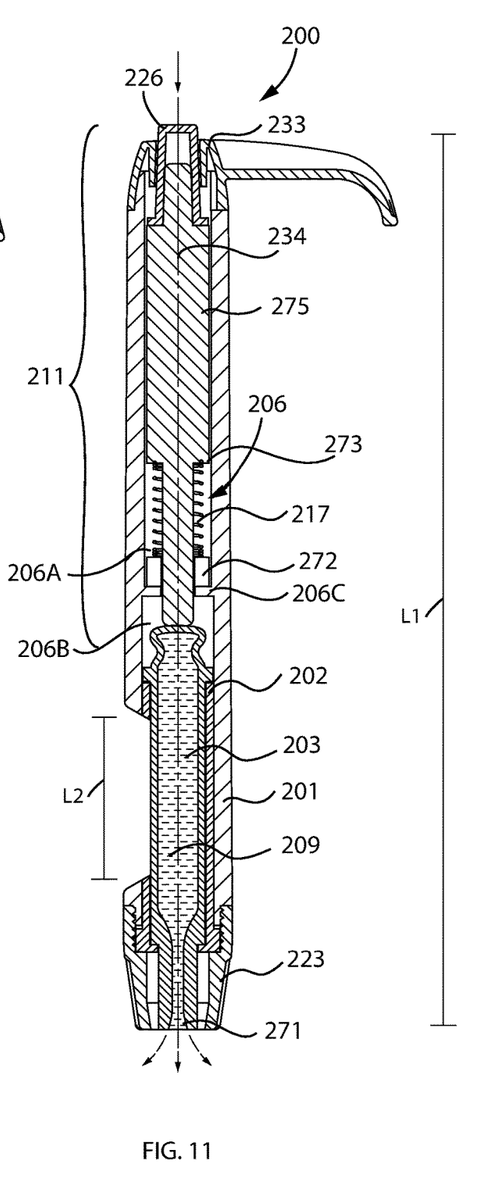
FIG. 11 is a cross-sectional view showing the actuator assembly at a depressed position wherein it compresses the ballonet and causes fluid to expel therefrom.
Figure 12:
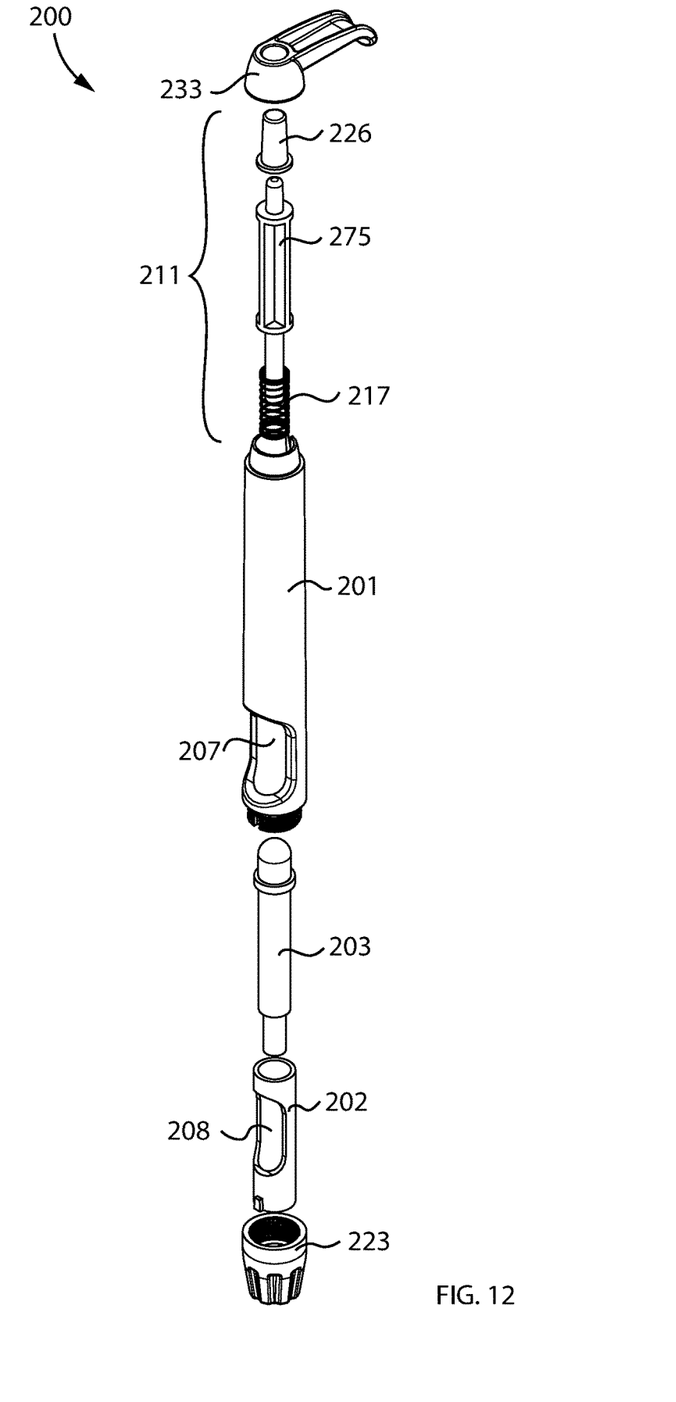
FIG. 12 is an exploded view of the multi-actuated micro-pipette controller shown in FIG. 5.

In a non-limiting exemplary embodiment, as perhaps best shown in FIGS. 5-6 and 12, first and second access ports 207, 208 permit direct user access to ballonet 203 without depressing press cap 226. In particular, a user directly squeezes ballonet 203 with his/her finger. Such a squeezing motion occurs along a travel path defined substantially transverse to the longitudinal axis 234 of primary housing 201 thereby causing air and/or fluid 209 to ingress/egress therefrom micro-pipette tip. In this manner, an operator may suction/expel fluid 209 via the micro-pipette tip by selectively depressing only the ballonet 203. Thus, ballonet 203 can be squeezed while seated at the secondary housing 202, as perhaps best shown in FIG. 13. Although FIG. 13 is an exploded view, it is noted that ballonet 203 is slidably and removably inserted within secondary housing 202.

In a non-limiting exemplary embodiment, as perhaps best shown in FIG. 14, the ballonet 203 and micro-pipette tip (similar to tip 14) can be removed from the primary housing 201 and secondary housing 202 and independently operated, without use of the actuator assembly 211, by directly squeezing ballonet 203.

While non-limiting exemplary embodiment(s) has/have been described with respect to certain specific embodiment(s), it will be appreciated that many modifications and changes may be made by those of ordinary skill in the relevant art(s) without departing from the true spirit and scope of the present disclosure. It is intended, therefore, by the appended claims to cover all such modifications and changes that fall within the true spirit and scope of the present disclosure. In particular, with respect to the above description, it is to be realized that the optimum dimensional relationships for the parts of the non-limiting exemplary embodiment(s) may include variations in size, materials, shape, form, function and manner of operation.

The Abstract of the Disclosure is provided to comply with 37 C.F.R. §1.72(b) and is submitted with the understanding that it will not be used to interpret or limit the scope or meaning of the claims. In addition, in the above Detailed Description, various features may have been grouped together or described in a single embodiment for the purpose of streamlining the disclosure. This disclosure is not to be interpreted as reflecting an intention that the claimed embodiment(s) require more features than are expressly recited in each claim. Rather, as the following claims reflect, inventive subject matter may be directed to less than all of the features of any of the disclosed non-limiting exemplary embodiment(s). Thus, the following claims are incorporated into the Detailed Description, with each claim standing on its own as defining separately claimed subject matter.

The above disclosed subject matter is to be considered illustrative, and not restrictive, and the appended claims are intended to cover all such modifications, enhancements, and other embodiment(s) which fall within the true spirit and scope of the present disclosure. Thus, to the maximum extent allowed by law, the scope of the present disclosure is to be determined by the broadest permissible interpretation of the following claims and their equivalents, and shall not be restricted or limited by the above detailed description.

What is claimed as new and what is desired to secure by Letters Patent of the United States is:

1. A multi-actuated micro-pipette controller for selectively transporting a volume of fluid, said multi-actuated micro-pipette controller comprising:
   a primary housing including
      an open proximal end and an open distal end axially opposed therefrom,
      a primary access port formed adjacent to said distal end, and
      a chamber extending from said open proximal end to said distal end such that said chamber is accessible from said primary access port;
   a secondary housing removably seated within said chamber, said secondary housing having a secondary access port at least partially aligned with said primary access port;
   a ballonet adapted to receive the fluid therein, said ballonet being removably inserted within said secondary housing and at least partially aligned with said secondary access port such that said ballonet is directly accessible and squeezable via said primary access port and said secondary access port; and
   an actuator assembly located at said primary housing and being operably engaged with said ballonet;
   wherein linear actuation of said actuator assembly compresses at least a portion of said ballonet and thereby causes the fluid to expel outwardly from said ballonet;
   wherein said primary housing has a centrally registered longitudinal axis axially aligned with said open proximal end and said open distal end, said primary access port and said secondary access port being axially offset from the centrally registered longitudinal axis;
   wherein said secondary housing is located adjacent to said open distal end of said primary housing and oppositely spaced from said open distal end of said primary housing;
   wherein said ballonet is oppositely spaced from said open proximal end of said primary housing.

2. The multi-actuated micro-pipette controller of claim 1, wherein said secondary housing is linearly inserted and retracted from said chamber of said primary housing during non-operating conditions.

3. The multi-actuated micro-pipette controller of claim 1, wherein said secondary housing remains statically nested within said chamber of said primary housing while said ballonet is compressed and released between tension and equilibrium positions, respectively.

4. The multi-actuated micro-pipette controller of claim 1, further comprising:
   a micro-pipette tip removably inserted into said open distal end of said primary housing and being in fluid communication with said ballonet.

5. The multi-actuated micro-pipette controller of claim 1, wherein, when said ballonet and said secondary housing are operably removed from said chamber of said primary housing, said ballonet and said secondary housing are operably disengaged from said actuator assembly such that the fluid is discharged outwardly away from said secondary housing by directly squeezing said ballonet positioned exterior of said primary housing.

6. The multi-actuated micro-pipette controller of claim 1, wherein, when said ballonet is operably removed from said secondary housing, the fluid is discharged outwardly away from said ballonet by directly squeezing said ballonet positioned exterior of both said primary housing and said secondary housing when said secondary housing is removed from said primary housing.

7. The multi-actuated micro-pipette controller of claim 1, wherein said primary access port and said secondary access port overlap along the longitudinal length of said primary housing.

8. The multi-actuated micro-pipette controller of claim 1, wherein said secondary housing remains spaced from said actuator assembly while said secondary housing and said ballonet are seated within said chamber of said primary housing.

9. The multi-actuated micro-pipette controller of claim 1, wherein said actuator assembly and said ballonet are oriented at an end-to-end configuration while seated within said chamber of said primary housing.

10. A multi-actuated micro-pipette controller for selectively transporting a volume of fluid, said multi-actuated micro-pipette controller comprising:
   a primary housing including
      a proximal end and a distal end axially opposed therefrom,
      a primary access port formed adjacent to said distal end, and
      a chamber extending from said proximal end to said distal end such that said chamber is accessible from said primary access port;
   a secondary housing removably seated within said chamber, said secondary housing having a secondary access port at least partially aligned with said primary access port;
   a ballonet adapted to receive the fluid therein, said ballonet being removably inserted within said secondary housing and at least partially aligned with said secondary access port such that said ballonet is directly accessible and squeezable via said primary access port and said secondary access port; and
   an actuator assembly located at said primary housing and being operably engaged with said ballonet;
   wherein linear actuation of said actuator assembly compresses at least a portion of said ballonet and thereby causes the fluid to expel outwardly from said ballonet;
   wherein said secondary housing is coaxially aligned with said primary housing while said secondary housing is disposed within said chamber;
   wherein each of said primary access port and said second access port is spaced from said proximal end and said distal end of said primary housing.

11. The multi-actuated micro-pipette controller of claim 10, wherein said secondary housing is linearly inserted and retracted from said chamber of said primary housing during non-operating conditions.

12. The multi-actuated micro-pipette controller of claim 11, wherein said secondary housing remains statically nested within said chamber of said primary housing while said ballonet is compressed and released between tension and equilibrium positions, respectively.

13. The multi-actuated micro-pipette controller of claim 12, further comprising:
a micro-pipette tip removably inserted into said distal end of said primary housing and being in fluid communication with said ballonet.

14. The multi-actuated micro-pipette controller of claim 10, wherein, when said ballonet and said secondary housing are operably removed from said chamber of said primary housing, said ballonet and said secondary housing are operably disengaged from said actuator assembly such that the fluid is discharged outwardly away from said secondary housing by directly squeezing said ballonet positioned exterior of said primary housing.

15. The multi-actuated micro-pipette controller of claim 10, wherein, when said ballonet is operably removed from said secondary housing, the fluid is discharged outwardly away from said ballonet by directly squeezing said ballonet positioned exterior of both said primary housing and said secondary housing when said secondary housing is removed from said primary housing.

16. The multi-actuated micro-pipette controller of claim 13, wherein said primary access port and said secondary access port overlap along the longitudinal length of said primary housing.

17. The multi-actuated micro-pipette controller of claim 16, wherein said secondary housing remains spaced from said actuator assembly while said secondary housing and said ballonet are seated within said chamber of said primary housing.

18. The multi-actuated micro-pipette controller of claim 17, wherein said actuator assembly and said ballonet are oriented at an end-to-end configuration while seated within said chamber of said primary housing.

19. A method of utilizing a multi-actuated micro-pipette controller for selectively transporting a volume of fluid, said method comprising the steps of:
obtaining a primary housing including a proximal end and a distal end axially opposed therefrom, a primary access port formed adjacent to said distal end, and a chamber extending from said proximal end to said distal end such that said chamber is accessible from said primary access port;
obtaining and removably seating a secondary housing within said chamber, said secondary housing having a secondary access port at least partially aligned with said primary access port, wherein said secondary housing is coaxially aligned with said primary housing while said secondary housing is disposed within said chamber;
obtaining a ballonet adapted to receive the fluid therein;
removably inserting said ballonet within said secondary housing and at least partially aligning said ballonet with said secondary access port such that said ballonet is directly accessible and squeezable via said primary access port and said secondary access port;
obtaining and locating an actuator assembly at said primary housing;
operably engaging said actuator assembly with said ballonet; and
causing the fluid to expel outwardly from said ballonet by linearly actuating said actuator assembly and thereby compressing at least a portion of said ballonet;
wherein each of said primary access port and said second access port is spaced from said proximal end and said distal end of said primary housing.

* * * * *